United States Patent [19]

Leyshon et al.

[11] Patent Number: 4,876,409
[45] Date of Patent: Oct. 24, 1989

[54] THIN BED COFEED REACTORS FOR METHANE CONVERSION

[75] Inventors: David W. Leyshon, West Chester; Robert A. Bader, Overbrook Hills, both of Pa.

[73] Assignee: Atlantic Richfield Company, Los Angeles, Calif.

[21] Appl. No.: 158,128

[22] Filed: Mar. 4, 1988

Related U.S. Application Data

[63] Continuation-in-part of Ser. No. 31,496, Mar. 30, 1987.

[51] Int. Cl.⁴ .............................................. C07C 2/00
[52] U.S. Cl. .................................... 585/500; 585/654; 585/656; 585/910

[58] Field of Search ............... 585/910, 911, 500, 654, 585/656, 943, 659

[56] References Cited

U.S. PATENT DOCUMENTS

| 3,223,746 | 12/1962 | Hammond | 585/910 |
| 4,654,458 | 3/1987 | Jezl | 585/500 |
| 4,754,094 | 6/1988 | Jubin | 585/500 |
| 4,754,095 | 6/1988 | Coughenour | 585/500 |

Primary Examiner—William R. Dixon, Jr.
Assistant Examiner—James M. Hunter, Jr.
Attorney, Agent, or Firm—William C. Long

[57] ABSTRACT

The invention relates to the conversion of methane to higher hydrocarbons by reaction of methane and gaseous oxidant under adiabatic conditions in a thin bed reactor, and to reactors for carrying out this reaction.

7 Claims, 4 Drawing Sheets

THIN BED COFEED REACTORS FOR METHANE CONVERSION

This is a continuation-in-part of co-pending application 07/031,496, filed Mar. 30, 1987.

FIELD OF THE INVENTION

The present invention relates to a method and apparatus for the conversion of methane to higher boiling hydrocarbons. In particular, the invention relates to certain adiabatic thin bed reactors, and to the conversion of methane to higher hydrocarbons by passing a relatively cool feed mixture containing methane and a gaseous oxidant such as molecular oxygen into a thin bed reactor, heating the feed gases in said reactor with heat generated by the methane conversion reaction to the reaction conditions effective to convert methane to higher hydrocarbons.

DESCRIPTION OF THE PRIOR ART

Methane is found in large quantities in gaseous form in somewhat remote regions of the world. The transportation of this methane to areas where it can be utilized is relatively inefficient.

Considerable work has been carried out relating to the conversion of methane to higher hydrocarbons which are readily condensable and which can be conveniently transported in liquid form. In this regard, reference is made to the following U.S. patents which are concerned with conversion of methane to higher hydrocarbons: U.S. Pat. Nos. 4,443,649; 4,444,984; 4,443,648, 4,443,645; 4,443,647; 4,443,644; 4,443,646; 4,499,323; 4,499,324; 4,593,139; 4,489,215; 4,499,322; 4,495,374; 4,544,784; 4,544,785; 4,547,610; 4,547,611; 4,517,398; 4,544,787; 4,547,608; 4,544,786; 4,568,785; 4,523,049; 4,523,050 and the like.

The conversion of methane to higher hydrocarbons in the presence of solids which may contain oxidative synthesizing agents as described in the above patents takes place effectively at elevated temperatures in the range of about 500° C. to 1200° C. The reaction is strongly exothermic in nature, and in order to properly regulate the reaction, to prevent excessive undesirable side reactions and to avoid an excessive temperature rise, it is necessary to remove the exothermic heat of reaction.

Problems particular to this conversion of methane include the fact that the reaction temperature is high enough to preclude or bring into serious question the use of many materials normally used in reactor construction The high temperatures result in rapid conversion of the reaction products to undesirable materials unless the residence time of the products at elevated temperatures is very short. Thus, high reaction space velocities and rapid quenching of the product are desirable.

Fixed bed reactors of the tubular or massive staged bed configuration have been considered for the reaction. However, such systems have not been satisfactory due to their cost and complexity, to pressure drop and materials of construction problems and to problems of heat removal and product degradation.

A further disadvantage of conventional fixed bed reactors is that the feed must be preheated to elevated temperatures. This requires fuel as well as an expensive, ceramically lined furnace.

SUMMARY OF THE INVENTION

In accordance with the present invention there is provided an improved method for continuous conversion of methane to higher hydrocarbons as well as apparatus especially suitable for carrying out the conversion The improved method involves the introduction of a feed gas mixture comprised of methane and gaseous oxidizing agent at a temperature well below reaction temperature into a reactor containing a solid contact agent. The depth of the reactor bed containing the contact agent is important, it must be relatively "thin", i.e. of a depth not exceeding about 20 inches and preferably not exceeding about 8 inches. The feed mixture is introduced into the reactor bed at a rate just sufficient to maintain the desired reaction - if the feed rate is too great the reactor bed will cool down and the reaction will be extinguished and if the rate is too low the reaction products will spend too much time in the reactor resulting in a loss of the desired product. In accordance with the invention, the reaction is carried out adiabatically, heat of reaction being used to heat the relatively cool feed gases to reaction temperature thus to moderate the reaction exotherm. Configuration of the reactor bed to permit appropriate flow of heat of reaction to preheat feed gases and cool the reaction zone is an essential feature of the invention.

In accordance with the present invention, methane is converted to higher hydrocarbons by contact with a solid contact agent in a reactor which is of a special design. In particular, the adiabatic reactor design and construction is such as to permit at least a substantial portion, i.e., at least 25% and preferably much more, of the heat of reaction to travel axially in a direction opposite to the flow of reaction gases and to preheat the reaction gases to the high temperatures necessary for the reaction. In addition, the transfer of heat prevents the catalyst from being damaged by excessive temperatures. In an advantageous practice, the reactor effectively comprises a relatively thin monolithic element having an oxidative synthesizing agent associated therewith, for example throughout or on the surfaces thereof, through which the feed gas containing methane and oxidant is passed at reaction conditions. In an even more advantageous practice, the reactor comprises a metal holder for the solid contact agent adapted to retain the contact agent in place while passing reaction gases into contact with the contact agent.

In accordance with the invention, relatively cold feed gas mixtures are rapidly heated in an adiabatic reactor to reaction conditions without complicated internals, without the necessity for a separate and costly preheating step, and without excessive catalyst temperatures. Preheating feed gases in this way effectively removes the heat of reaction and provides means of controlling the reaction. The use of a thin bed also minimizes pressure drop and facilitates rapid effluent quenching.

Unlike conventional tubular or staged reactors, this reactor has no gas tight seals above 250° C., making it practical to operate it at pressures of 100 psig or higher. This greatly reduces compression costs downstream.

BRIEF DESCRIPTION OF THE DRAWINGS

The accompanying drawings illustrate the invention.

Accompanying

Accompanying

Accompanying

Accompanying

Accompanying

Accompanying

DETAILED DESCRIPTION OF THE INVENTION

In accordance with the present invention, a relatively cool reaction feed gas containing both methane and an oxidant is passed into contact with a contact solid which is a reducible or non-reducible metal oxide in an adiabatic thin bed reactor at conditions of elevated temperature, whereby the methane reacts to form higher hydrocarbons and coproduct water.

In practice of the invention, a reaction feed gas comprised of both methane and oxidant is provided. In addition to methane the hydrocarbon feedstock employed in the method of this invention may contain other hydrocarbon or non-hydrocarbon components. The methane content of the hydrocarbon portion of the feedstock, however, will typically be within the range of about 40 to 100 vol. %, preferably within the range of about 80 to 100 vol. %, more preferably within the range of about 90 to 100 vol. %.

The oxidant gas preferably comprises molecular oxygen; other gases such as nitrogen and carbon oxides may be present. Oxides of nitrogen such as $N_2O$ can be employed but are more costly.

The use of certain materials such as chalcogens and halogens in the feed also promotes the desired reaction as does the presence of steam as set forth in copending application 07/014405 filed Feb. 13, 1987.

The ratio of hydrocarbon feedstock to oxidant gas is not narrowly critical to the present invention. Generally, it is desirable to keep the hydrocarbon/oxygen molar ratio high enough to avoid the formation of gaseous mixtures within the flammable region and low enough to obtain 20 to 30% methane conversion. It is preferred to maintain the volume ratio of hydrocarbon/oxygen within the range of about 1-100:1, more preferably within the range of about 2-50:1. Methane/air feed mixtures containing about 20 to 70 volume % methane have been found to comprise a desirable feedstream. Further dilution of the feedstream with gases such as steam, although beneficial, is not necessary to practice of the invention.

It is a feature of the subject invention that the gas mixture fed to the reactor is at a temperature substantially below reaction temperature, i.e., at least 100° C. below reaction temperature and preferably at least 400° C. below reaction temperature. The reaction is carried out adiabatically essentially no external heating or cooling is provided. The reaction is carried out in a thin bed, i.e., a bed of solid contact agent having a depth of less than 20 inches, preferably less than 8 inches.

An essential feature is that the configuration of the reactor bed must be such to permit effective flow of heat of reaction axially in a direction opposite the flow of reaction gases thus to preheat the relatively cool feed gases to reaction temperature in the reaction bed by transfer of the heat of reaction.

Figures 4, 5:
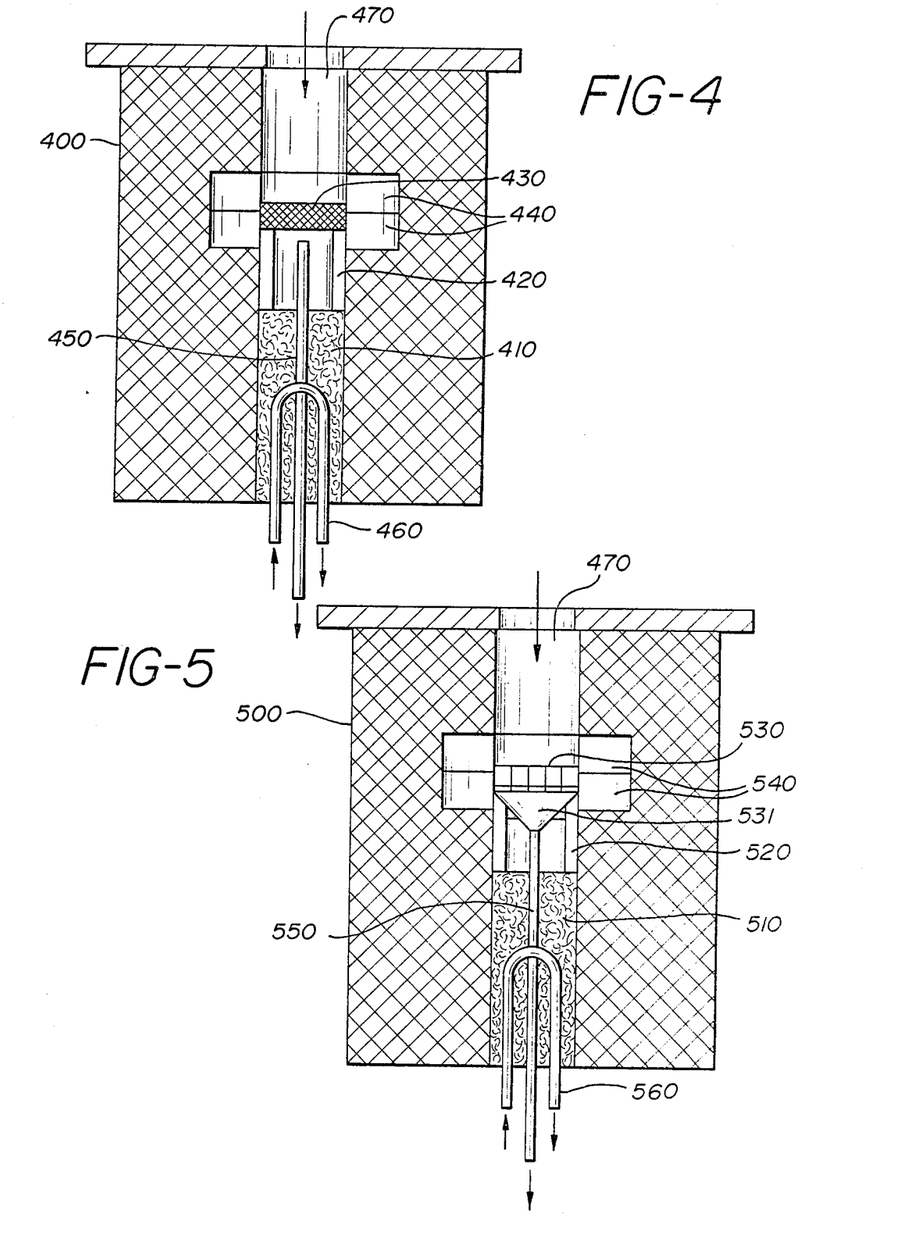
FIG. 4 illustrates in schematic form a reactor of the invention.
FIG. 5 illustrates an alternative embodiment where in place of the monolithic element of FIG. 4 an element comprised of bonded tubes containing particles of solid contact agent is employed.

A suitable fixed reactor bed configuration is that of a monolith having a honeycomb configuration with a reducible metal oxide oxidative synthesizing agent coated on surface thereof or distributed throughout, the monolithic reactor bed being capable of transmitting heat of reaction by solids conduction axially countercurrent to the flow of reaction gases. Configurations which can also be suitably employed in this invention include packed beds of particles such as discrete spheres comprised of contact agent provided the bed height is sufficiently low and the particle size sufficiently large. Eddys and turbulence in such beds provide the effective axial heat transfer necessary to sustain the reaction. Advantageously, inplace of a single packed bed configuration, a number of tubes of high heat conducting material such as alumina, stainless steel, and the like can be bonded together and filled with the particles of the solid contact agent. This is illustrated in FIG. 5.

In the most preferred practice, however, metal such as stainless steel in the desired reactor bed thickness is used as a holder for the particles of contact agent, the contact agent being placed, for example, in holes drilled in a sheet of the metal through which reaction gases are passed. This is illustrated in FIG. 6.

In order to accomplish the objectives of the invention, the effective thermal conductivity of the reactor bed must be at least $1 \times 10^{-5}$ cal/sec-°C.-cm, and is preferably at least $5 \times 10^{-4}$ cal/sec-°C.-cm The fixed reactor bed may be metallic, non-metallic, semi-conducting or a combination. Suitable thermal conductivity can be insured by appropriate selection of the primary material used or where thermal conductivity is unsuitably low it can be enhanced by the provision of solid pieces of more conductive materials in the reactor bed.

Figure 1A:
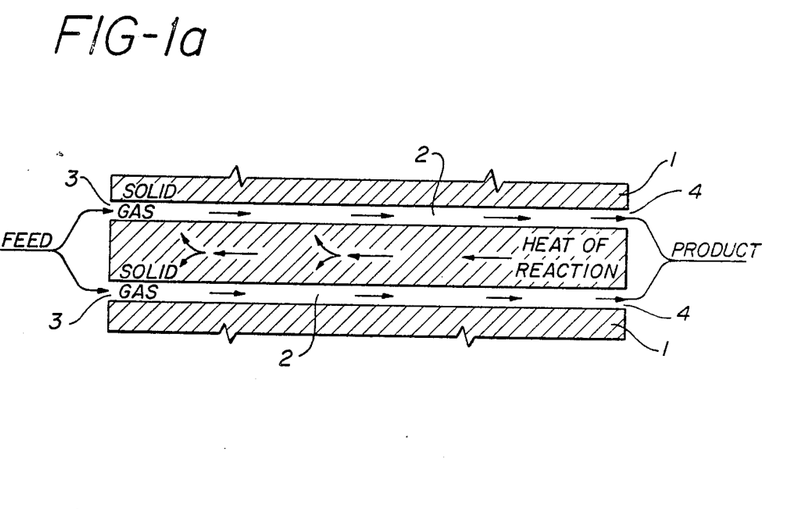
FIG. 1 illustrates in diagrammatic form the principles of operation of a preferred embodiment of the invention.

The invention can, perhaps, be better explained by reference to FIG. 1. FIG. 1a depicts in schematic form a portion of a monolithic reactor bed while FIG. 1b is a graphic presentation of the temperature profile of the reactor portion of FIG. 1a.

Referring to FIG. 1a, the solid monolithic reactor 1 has channels 2, therethrough for the passage of reaction gases. The feed gases comprised of methane and oxidant at a temperature well below reaction temperature are introduced into channels 2 at inlet 3, reaction product gases at the elevated reaction temperatures are removed from channels 2 at exit 4.

Figure 1B:
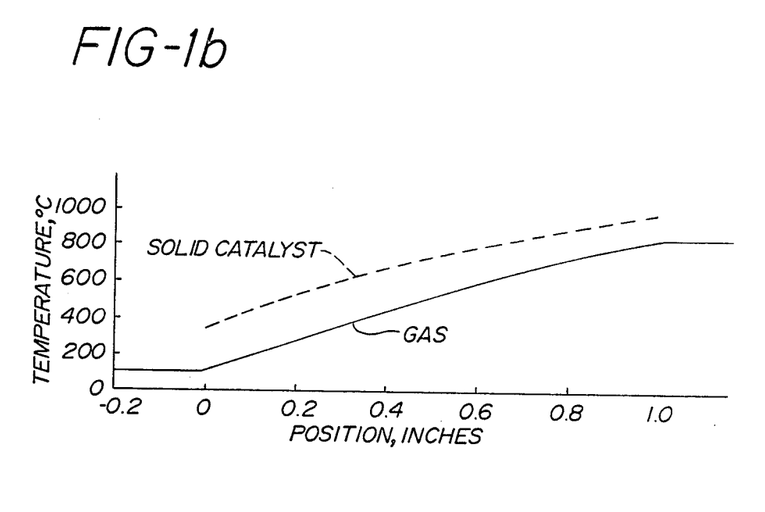

With reference to FIG. 1b, it can be seen that as the feed gases pass through channels 2 they are heated by heat of reaction conducted axially through solid 1 in a direction opposite to the gas flow to a sufficiently high temperature such that the gases undergo the desired conversion of methane to higher hydrocarbons. As above indicated, this desired reaction takes place at temperatures in excess of about 500° C., preferably above 600° C.

The system depicted in FIG. 1 can be considered as comprised of two zones, a first preheat zone and a later reaction zone. There is no sharp demarcation between these zones—i.e. the feed gases may begin reacting while still being heated to higher reaction temperature. The cool feed gases upon reaching reaction temperature undergo the exothermic conversion to the desired products, the heat of reaction thus generated flowing axially to preheat additional feed gases.

FIG. 1b shows postulated gas and solid temperature profiles over the one inch reactor bed. It will be appreciated that the reactor is adiabatic—i.e. essentially no external heating or cooling is provided.

The solid contact materials used in the methane conversion of this invention are of the type previously known and described for the oxidative conversion of methane to higher hydrocarbons.

Solids useful in the present invention include those characterized as "nonacidic". This description is meant to refer to the main, predominant surface properties of the nonacidic solids. For example some solid bases are known to have acidic properties to some extent. See Tanabe, K., "Solid Acid and Base Catalysts." In: Catalysis Science & Technology, Vol. 2 (New York, Springer-Verlag Berlin Heidelberg, 1981). Currently preferred nonacidic solids used in the present process are characterized by negligible acidity (less than about 0.01 meg/gm) in the $H_o$ range less than about 3.3, preferably less than about 6.8. $H_o$ is the Hammett acidity parameter described on pp. 234–241 of Tanabe.

A further characteristic of preferred nonacidic solids for the present process is a relatively low surface area. Nonacidic solids having surface areas less than about 50 cm$^2$/gm are suitable, but the surface areas of preferred solids are within the range of about 0.1–10 m$^2$/gm.

In one distinct embodiment of this invention, methane and a gaseous oxidant are contacted with a non-acidic solid characterized by the substantial absence of reducible metal oxides. Characteristics of nonacidic acids preferred for this embodiment are that they be stable and substantially nonreducible under process conditions. Examples of suitable nonacidic solids include those solid bases described in Table 2 on p. 233 of Tanabe, supra. However, presently preferred nonacidic solids are metal oxides and mixed oxides. Alkaline earth oxides are particularly preferred, especially MgO and CaO. Other suitable ceramics are SiO$_2$, alpha-Al$_2$O$_3$, La$_2$O$_3$, ThO$_2$, TiO$_2$, SiC, and ZrO$_2$. Such materials are relatively stable under the conditions of the present process.

Alkali metal-promoted alkaline earth oxides are preferred nonacidic solids for this embodiment. Such solids are described and exemplified in commonly-assigned U.S. patent application Ser. No. 06/738,110, filed May 24, 1985, the entire content of which is incorporated herein by reference. Halogen and/or chalcogen promotors may be employed; see commonly-assigned U.S. Pat. No. 4,634,800, the entire content of which is incorporated herein by reference.

In another distinct embodiment of this invention, methane and a gaseous oxidant are contacted with solid comprising a reducible metal oxide. While such solids are sometimes referred to as "catalysts" it will be understood that, under conditions of use, nonacidic solids comprising a reducible metal oxide act as selective oxidants, and, therefore, take on the characteristics of a reactant during use. Thus, for example, the term "Mn-containing oxides" is meant to embrace both reducible oxides of Mn and reduced oxides of Mn, it being understood reducible oxides comprise the principal active component of the compositions.

In their active state, such catalysts comprise at least one reducible oxide of at least one metal, which oxide when contacted with methane at synthesizing conditions (e.g., at a temperature within the range of about 500° to 1000° C.) produces higher hydrocarbon products, coproduct water, and a reduced metal oxide. The term "reducible" is used to identify those oxides of metals which are reduced under the aforesaid conditions. The term "reducible oxides of metals" includes: (1) compounds described by the general formula M$_x$O$_y$ wherein M is a metal and x and y designate the relative atomic proportions of metal and oxygen in the composition and/or (2) one or more oxygen-containing metal compounds (i.e., compounds containing elements in addition to the metal and O), provided that such oxides and compounds have the capability of producing higher hydrocarbon products from methane as described herein.

Effective agents for the conversion of methane to higher hydrocarbons have previously been found to comprise reducible oxides of metals selected from the group consisting of manganese, tin, indium, germanium, antimony, lead, bismuth and mixtures thereof. See U.S. Pat. Nos. 4,443,649; 4,444,984; 4,443,648; 4,443,645; 4,443,647; 4,443,644; and 4,443,646. Reducible oxides of manganese are particularly preferred catalyst components.

Reducible oxides of cerium, praseodymium, and terbium have also been found to be effective for the conversion of methane to higher hydrocarbons, particularly associated with an alkali metal component and/or an alkaline earth metal component. See U.S. Pat. Nos. 4,499,324 (Ce) and 4,499,323 (pr) and also see commonly-assigned U.S. patent application Ser. No. 06/600,918 (Tb).

Reducible oxides of iron and ruthenium are also effective, particularly when associated with an alkali or alkaline earth component. See commonly-assigned U.S. patent application Ser. No. 06/600,730 (Fe) and U.S. Pat. Nos. 4,489,215 and 4,593,139 (Ru).

Alkali and alkaline earth metals and compounds thereof have been found to improve the hydrocarbon product selectivity of reducible metal oxides. The further incorporation of phosphorus into solids promoted by alkali or alkaline earth components enhances catalyst stability. See commonly-assigned U.S. Pat. Nos. 4,499,322 and 4,495,374, the entire content of which are incorporated herein by reference. Alkali metals are selected from the group consisting of lithium, sodium, potassium, rubidium, and cesium. Lithium, sodium and potassium, and especially lithium and sodium, are preferred alkali metals. Alkaline earth metals are selected from the group consisting of magnesium, calcium, strontium and barium. Presently preferred members of this group are magnesium and calcium. Compositions derived from magnesia have been found to be particularly effective catalytic materials. Boron and compounds thereof are also desirably present in the reducible metal oxide catalyst employed in the process of this invention. See commonly-assigned U.S. patent application Ser. No. 06/877,574, entire content of which is incorporated herein by reference. One class of boron promoted compositions useful in the process of this invention comprises:

(1) at least one reducible metal oxide,
(2) at least one member of the group consisting of boron and compounds thereof, and
(3) at least one member of the group consisting of oxides of alkaline earth metals.

A related class of catalyst compositions further comprises at least one alkali metal or compound thereof.

Sodium and lithium are preferred alkali metal components.

One further, special class of catalyst compositions useful in the process of this invention are mixed oxides of sodium, magnesium, manganes and boron characterized by the presence of the crystalline compound $NaB_2Mg_4Mn_2O_x$ wherein x is the number of oxygen atoms required by the valence states of the other elements, said compound having a distinguishing x-ray diffraction pattern. In its most active form, the compound is believed to correspond to the formula $NaB_2Mg_4Mn_2O_{11}$. While this crystalline compound has been found to be associated with highly effective oxidant compositions, it has further been found that still better results are obtained when the oxidant is characterized by both: (1) the presence of crystalline compound $NaB_2Mg_4Mn_2O_x$ and (2) a stoichiometric excess of Mn relative to at least one of the other elements of the crystalline compound. In currently preferred oxidants of this type, a stoichiometric excess of Mn relative to B is provided. In a still more specific preferred embodiment excess amounts of Na and Mg, as well as Mn, are present in the mixed oxide composition relative to the amounts required by the amount of boron present to satisfy the stoichiometry of the compound $NaB_2Mg_4Mn_2O_x$.

Further examples of components which may be present in the catalysts used in the process of this invention are halogen and chalcogen components. Such components may be added either during preparation of the catalysts or during use. Methane conversion processes employing halogen-promoted reducible metal oxides are disclosed in U.S. Pat. No. 4,544,784. Methane conversion processes employing chalcogen-promoted, reducible metal oxides are disclosed in U.S. Pat. No. 4,544,785.

The reducible metal oxides compositions may be supported by or diluted with support materials such as silica, alumina, titania, zirconia and the like, and combinations thereof. When supports are employed, alkaline earth oxides, especially magnesia, are preferred.

The catalysts are conveniently prepared by any of the methods associated with similar compositions known in the art. Thus, such methods as precipitation, co-precipitation, impregnating, granulation, spray drying or dry mixing can be used. Supported solids may be prepared by methods such as adsorption, impregnation, precipitation, co-precipitation, and dry-mixing. For example, compounds of Mn, Sn, In, Ge, Pb, Sb, Bi, Pr, Tb, Ce, Fe and/or Ru may be combined with compounds of other components in any suitable way. Substantially any compound of the components can be employed. Compounds typically used would be oxides or organic or inorganic salts of the recited components.

To illustrate, when preparing a catalyst containing: (1) a reducible metal oxide component (e.g., Mn), (2) an alkali metal component, (3) a boron component and (4) an alkaline earth component; one suitable method of preparation is to impregnate compounds of the fourth component of the composition with solutions of compounds of Mn, alkali metals, and/or boron. Suitable compounds for impregnation include the acetates, acetyl acetonates, oxides, carbides, carbonates, hydroxides, formates, oxalates, nitrates, phosphates, sulfates, sulfides, tartrates, fluorides, chlorides, bromides, or iodides. After impregnation, the preparation is dried to remove solvent and the dried solid is calcined at a temperature selected within the range of about 100° to 1200° C. Particular calcination temperatures will vary depending on the compounds employed. Preferably, the alkaline earth component is provided as the oxide. Preferably, the alkali metal component is provided as a basic composition of the alkali metal(s). Examples are sodium hydroxide, sodium acetate, lithium hydroxide, lithium acetate, etc. When P is employed as an additive, it has been found desirable to add the alkali metal and P to the composition as compounds such as the orthophosphates, metaphosphates, and pyrophosphates of alkali metals. Pyrophosphates are preferred. Sodium pyrophosphate is particularly preferred. Preferably, the boron component is provided as boric acid, boric oxide (or anhydride), alkali metal borates, boranes, borohydrides, etc., especially boric acid or oxide.

Formation of the crystalline compound $NaB_2Mg_4Mn_2O_x$ may be accomplished by reacting active compounds of the substituent elements. A suitable mixture of the reactive compounds is formed and heated for a time sufficient to form the crystalline material. Typically, a temperature of about 850° to about 950° C. is sufficient. When preparing mixed oxide compositions characterized by the presence of other crystalline compounds, the composition is desirably incorporated with binders or matrix materials such as silica, alumina, titania, zirconia, magnesia and the like.

Regardless of which particular catalyst is prepared or how the components are combined, the resulting composite will generally be dried and calcined at elevated temperatures prior to use. Calcination can be done under air, $H_2$, carbon oxides, steam, and/or inert gases such as $N_2$ and the noble gases.

A suitable embodiment of the invention is illustrated in accompanying FIG. 2. In this embodiment the reactor bed is a relatively thin monolithic honeycomb with the oxidative synthesizing agent dispersed throughout. The monolithic structure is preferably comprised of a substantially continuous ceramic material having suitable strength and thermal conductivity such as alumina, magnesia, cordierite, zirconia, zirconia-spinel, silicon-carbide, lithium aluminosilicates, and the like.

Figure 2A:
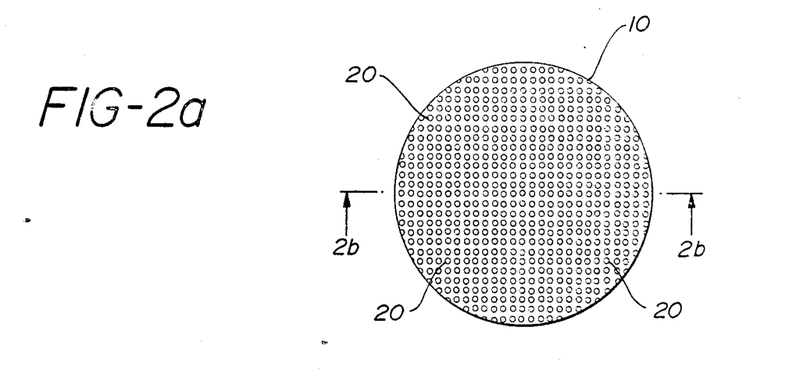
FIG. 2 illustrates two views of a suitable monolithic reactor element which can be employed in the invention.
Figure 2B:
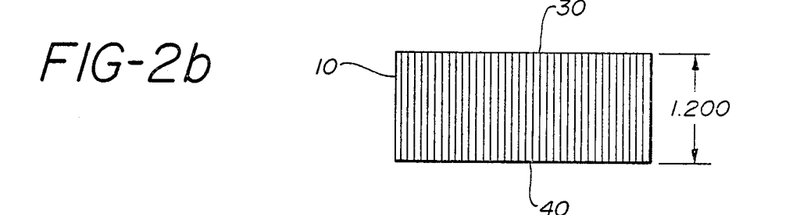

Referring to FIG. 2, there is shown in FIG. 2a a top view of a thin bed monolithic reactor, while in FIG. 2b a sectional view of the reactor is depicted. The thickness of the monolithic reactor can range from about 0.2 to about 20 inches but is preferably between 0.5 inches and 3 inches in thickness.

It is important to provide sufficient wall thickness relative to the opening dimensions such that adequate flow of the heat of reaction through the solid is maintained. Structurally the monolith should have sufficient wall thickness relative to the diameter of the passages to insure adequate structural integrity at reaction conditions while providing sufficient heat transfer capacity for effective reaction preheat and control. Generally speaking, wall thickness of the monolith cell should be at least as great as the effective diameter of the cell passages.

In especially preferred practice, the ratio of monolith cell wall thickness to diameter of the monolith cell passages should be in the range of about 1 to 10, and preferably 1.5 to 5, and the cell passage diameter should be 0.15 inches or less, preferably 0.01 to 0.04 inches.

As above mentioned, the thermal conductivity of the monolith should be at least $1 \times 10^{-5}$ cal/sec-°C.-cm in order that the reactor structure function effectively to preheat feed gases while at the same time moderating the reaction exotherm. Preferably the thermal conductivity is at least $5 \times 10^{-4}$ cal/sec-°C.-cm.

As shown in FIG. 2a, the monolithic reactor bed 10 is circular in shape and contains a plurality of passages 20 through which the reaction gas mixture passes. As shown in FIG. 2b the reaction gas mixture of methane and oxidant enters the monolith passages at 30 and is immediately heated to reaction temperature by exothermic reaction heat conducted axially through the monolith countercurrent to the gas flow. During the subsequent passage through the monolithic reactor, methane is converted to higher hydrocarbons. An oxidative synthesizing agent is provided either as an integral part of the monolithic structure or as a deposit on the passage surfaces to promote conversion of the methane to the higher hydrocarbons. The reaction mixture exits the monolithic reactor at 40 and is rapidly quenched to prevent excessive side reactions.

The reactor bed need not be circular, other configurations can be employed. In particularly preferred practice, the monolith can be comprised of a plurality of elements, e.g., 6 inch squares which can be adhered to each other to provide the desired overall configuration.

An alternative embodiment is illustrated in FIG. 5. In this Figure, the monolithic element 430 in FIG. 4 is replaced with element 530 which is comprised of a plurality of ceramic or metal tubes which are bonded together and which are filled with particles of the solid contact agent. This embodiment has the advantage over reactor systems where a thin bed of particles of contact agent is used without the plurality of tubes in that the tubes provide increased heat transfer throughout the bed thus facilitating adiabatic operation.

Attached FIG. 6 illustrates the preferred embodiment of the invention wherein the reactor bed is comprised of a metal holder.

Figure 6A:
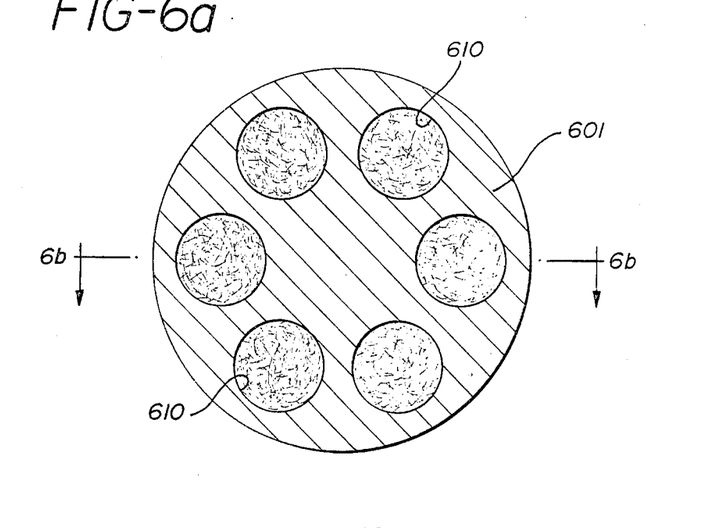
FIG. 6 illustrates a further alternative embodiment of the reactor element wherein a metal contact solid holder is employed.

FIG. 6a is a top view wherein stainless steel sheet 601 having the desired thickness has drilled therethrough a plurality of passages 610 adapted to contain solid particles 620 of the contact agent and permit passage therethrough of reaction gases.

Figure 6B:
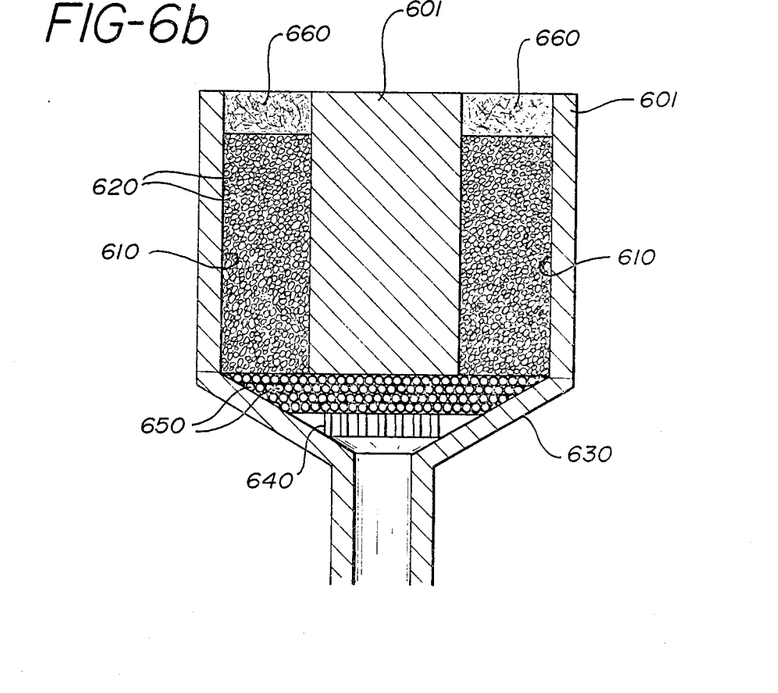

FIG. 6b is an elevation view of the reactor showing the contact agent particles packed in passages 610. In the embodiment shown, support means for the contact agent particles comprise inverted cone 630 containing support grid 640. Inert spheres 650 rest on the support grid and in turn support contact agent particles 620. Quartz wool 660 is placed in the upper portion of passages 610 to prevent loss of contact solid particles.

Use of the reactor configuration shown in FIG. 6 is especially advantageous. Costs of forming particulate contact solid are much less than that of forming monolithic catalyst elements. The metal contact agent holder can provide the axial heat transfer necessary without a measurable selectivity penalty. Use of the metal holder relative to use of ceramics is advantageous in that the reactor is less expensive because metal can be welded and machined, unlike ceramics; reliability is improved since metals are less likely to fracture; replacement is easier because conventional disassembly techniques can be used; the thermal conductivity and heat capacity per unit volume of metals such as stainless steel are far higher than most ceramics resulting in significantly improved temperature control.

The methane and oxidant feed gas mixture is passed into contact with solid oxidative synthesizing agent in the thin bed reactor suitably without preheating. Upon contact with the reactor the feed gases are very rapidly heated by the exothermic reaction to elevated temperature effective for accomplishing the desired methane conversion reaction. Generally speaking, reaction temperatures in the range of 500° to 1200° C. are appropriate.

Operating temperatures for contacting the methane with the contact agent are preferably selected within the range of about 500° to about 1000° C.; the particular temperature selected depending upon the particular reducible metal oxide(s) employed in the contact art. For example, reducible oxides of certain metals may require operating temperatures below the upper part of the recited range to minimize sublimation or volatilization of the metals (or compounds thereof) during the methane contact. Examples include reducible oxides of indium, germanium and bismuth (operating temperatures will preferably not exceed about 860° C.).

Operating pressures for the methane contacting step are not critical to the presently claimed invention. However, both general system pressure and partial pressure of methane have been found to effect overall results. Preferred operating pressure are within the range of about 0.1 to about 30 atmospheres. The partial pressure of methane in the reaction zone is preferably maintained within the range of about 0.3 atmosphere to about 8 atmospheres.

The space velocity of the gaseous reaction streams are similarly not critical to the presently claimed invention, but have been found to affect overall results. Preferred total gas hourly space velocities are within the range of about 2000 to 100,000 hr.$^{-1}$, more preferably within the range of about 4000 to 80,000 hr.$^{-1}$.

The effluent from the contact zone contains higher hydrocarbon products (e.g., ethylene, ethane and other light hydrocarbons), carbon oxides, water, unreacted hydrocarbon (e.g., methane) and oxygen, and other gases present in the oxygen-containing gas fed to the contact zone. Higher hydrocarbons may be recovered from the effluent and, if desired, subjected to further processing using techniques known to those skilled in the art. Unreacted methane may be recovered and recycled to the contact zone.

Figure 3:
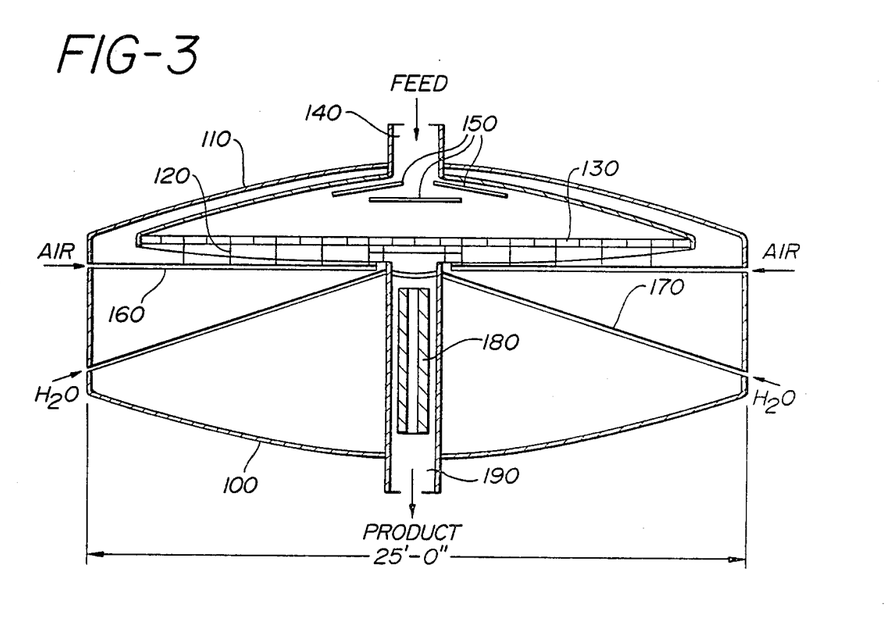
FIG. 3 illustrates in schematic form an overall reactor configuration incorporating the monolithic element.

FIG. 3 illustrates an overall reactor structure comprised of the thin reactor bed of the invention. Referring to FIG. 3, there is provided a commercial sized reactor having 25 foot diameter metal shell 100 with removable lid 110. Mechanical support means 120 are provided to support monolithic thin reactor bed 130 which in turn is comprised of 6 inch square pieces of monolith glued together. The bed has an overall diameter of 20 feet, and a thickness of 1.5 inches. Each 6 inch square element has 1400 holes of 0.035 inch diameter for the passage of reaction gas therethrough.

The feed gas mixture of methane and oxidant enters via conduct 140 and is distributed by baffles 150 across the reactor bed.

The feed temperature is set by the heat of reaction, the diluent concentration and the desired outlet temperature. In any event, it is essential that the feed gases to the reactor bed be at least 100° C. cooler than the product mixture exiting the bed. Preferably this differential is at least 400° C.

The monolithic elements are prepared as described in Example 1 following. In order to start the reaction there is provided air and burner means at 160 effective to bring the reactor bed up to the 500°–1200° C. reaction temperature. Other means may also be employed to heat the bed.

Once this bed temperature has been established the reaction becomes self-sustaining as the inlet gases are preheated by heat of reaction conducted axially through the bed.

Water quench is provided via lines 170 and the product gases exit over heat recovery boiler tubes 180 and are removed through conduit 190.

It should be noted that in any of the desired practices of the invention, heating means are provided during start up of the operation to heat the reactor bed to sufficiently high temperature that methane and oxidant will react upon introduction into the bed. Thereafter, the heating means are not employed and the reaction is sustained by the heat of reaction released.

EXAMPLE 1

Referring to FIG. 4, there is shown a thin bed reactor containing a solid monolithic element bed according to the invention.

A 10" schedule 80 pipe designated 400 is used as the reactor shell. Inside the shell is positioned a 3.5 inch O.D. 3.125 inch I.D. alumina tube 410 sealed at the bottom to isolate reaction gases from the metal shell. Alumina ring 420 is positioned inside tube 410 to provide support for monolithic reactor catalyst element 430.

Two 1500 watt cylindrical start-up heaters 440 are provided in order to preheat the catalyst bed to reaction temperature before introduction of the methane/oxidant gas mixture. Insulation is provided in the annular space between shell 400 and alumina tube 410 which aids in supporting heaters 440.

Product tube 450 is provided for withdrawing the reaction gas product mixture. Tube 450 extends to within about 0.5 inches of monolithic catalyst element 430 and at the bottom is sealed within alumina tube 410. Water cooling coils 460 are provided to aid in quenching the reaction product mixture.

In the runs according to this example, the monolithic catalyst element is 3.125 inches in diameter with a bed height of 1.1 inches. The element weighs 125 grams and is prepared as follows:

About 63.50 parts by weight MgO, 6.86 parts by weight LiOH, 17.72 parts by weight $H_3BO_3$ and 43.68 parts by weight $Mn_3O_4$ are ball milled for three hours. To the mixture is added sufficient water to form paste which retains a punched hole. Upon water addition an exotherm occurs which dries the mixture within an hour. Prior to drying, the paste is placed in a mold where it is formed into a monolithic element having the desired dimensions and the appropriate number of holes (channels) of the desired diameter are formed.

After 2-3 hours drying at ambient conditions, the monolithic element is calcined at 950° C. for 16 hours to form the finished element.

Channels for the passage of the gases through the monolithic element number 125 per inch$^2$ and each has an 0.045 inch diameter. The monolith has a thermal conductivity (at 850° C.) of $5.8 \times 10^{-4}$ cal/sec-°C.-cm.

Feed gases enter via 470, are preheated and react in monolithic element 430, and exit via product line 450. Thermocouples are provided (not shown) at a number of locations in the monolithic element 430.

The reaction gas mixture is composed by volume of 50% methane and 50% air. A flow of 7 liters per minute each of methane and air at room temperature is maintained.

Initially the methane and air mixture is bypassed around the reactor and nitrogen is introduced at the rate of 100 cc/min. via 470 and passes through monolithic element 430 and into line 450 while the monolithic element is electrically preheated by means of heater 440.

When the temperature of the monolith reaches about 760°–870° C., the reaction is commenced by diverting the bypassed methane and air flows into the reactor; at this time the heaters are set for adiabatic conditions. No back pressure regulator is used so that the reaction is carried out at ambient pressure.

Oxygen concentration in the exit gas is measured and a drop in oxygen concentration lasting over 25 minutes is observed indicating a sustained reaction. Temperature of the monolithic element increases slightly, rising about 25° C. over 4 minutes.

The product mixture sampled at 7 minutes run time is shown in Table 1.

TABLE 1

| Conversion % | | Selectivity % | | | | | | |
|---|---|---|---|---|---|---|---|---|
| $O_2$ | Methane | $C_2=$ | $C_2$ | $C_3$ | $C_4^+$ | CO | $CO_2$ | $\Sigma C_2^+$ |
| 69.8 | 15.1 | 33.2 | 9.8 | 4.4 | 3.4 | 26.5 | 22.7 | 50.8 |

EXAMPLE 2

The reactor used is the same as that shown above except a different monolithic catalyst element is used. This element has the same diameter and channel size as that above but has a depth of 1.3 inches, a weight of 160 grams and has 40 channels per inch$^2$. The element was prepared essentially as described above and has the same chemical composition and channel composition.

The same gas flows are employed as in Example 1 but a back pressure regulator is used, set to maintain reactor pressure at 30 psig.

A drop in oxygen concentration in the exit gas is observed indicating a sustained reaction and product sampled at 20 minutes run time is shown in Table 2.

TABLE 2

| Conversion % | | Selectivity % | | | | | | |
|---|---|---|---|---|---|---|---|---|
| $O_2$ | Methane | $C_2=$ | $C_2$ | $C_3$ | $C_4^+$ | CO | $CO_2$ | $\Sigma C_2^+$ |
| 99+ | 21.6 | 34.2 | 4.1 | 5.0 | 11.4 | 19.4 | 25.9 | 54.7 |

In the examples described above, it is possible to further improve the heat conductivity of the catalyst element and thus reaction selectivity by incorporating in the element materials which do not adversely affect the reaction and which have relatively high heat conductivity. In selecting such materials it is important that the material itself be stable under reaction conditions and preferably that the material have thermal expansion characteristics similar to that of other components of the catalyst element. Especially preferred materials are fused alumina and magnesia. These materials can be readily obtained in the form of rods having the same diameter as the channels of the monolithic element. These rods can be inserted in a selected number of the channels to provide continuous heat conducting elements within the monolith and to improve the overall heat conductivity to the desired extent.

EXAMPLE 3

The reactor used above was modified by replacement of the monolithic catalyst element with 140 grams $7 \times 20$ mesh catalyst particles supported by alumina. The catalyst has the composition and method of preparation as described for Example 1 except that it is ground and sifted.

Preheat and gas flows are as above and the reactor operated at ambient pressure. Exit oxygen concentrations dropped during the run indicating sustained reaction. Product sampled at 19 minutes run time is shown in Table 3.

TABLE 3

| Conversion % | | Selectivity % | | | | | | |
|---|---|---|---|---|---|---|---|---|
| $O_2$ | Methane | $C_2=$ | $C_2$ | $C_3$ | $C_4+$ | CO | $CO_2$ | $\Sigma C_2+$ |
| 99+ | 23.5 | 35.8 | 5.5 | 5.2 | 6.4 | 17.6 | 29.5 | 52.9 |

EXAMPLE 4

Although it is possible to operate a packed bed adiabatically, as in Example 3, it is difficult to control the temperatures in the catalyst bed. Thermocouples within the bed at one depth show some temperatures rise rapidly while others fall. This situation is greatly improved by the addition of solid heat pipes to the catalyst bed. These provide some heat capacity to stabilize the temperatures and they assist in transferring heat upstream to preheat the feed. The net effect is that the catalyst temperatures are brought closer together at the same level in the bed. The catalyst bed still has a large temperature gradient from top to bottom, as is necessary.

Referring to FIG. 5, there is shown a thin bed reactor containing solid contact agent particles ground to 8 to 14 mesh and placed in 6 one inch O.D. by 0.75 inch I.D. alumina tubes 3.5 inches in length cemented in a bundle using Babcock and Wilcox HDHS-98 refractory.

A 10" schedule 80 pipe designated 500 is used as the reactor shell. Inside the shell is positioned a 3.5 inch O.D. 3.125 inch I.D. alumina tube 510 sealed at the bottom to isolate reaction gases from the metal shell. Ring 520 is positioned inside tube 510 to provide support for the catalyst containing tube bundle 530. Catalyst particles are maintained in the tubes by a fiberous ceramic pad resting on a funnel cast from HDHS-98 (531).

Two 1500 watt cylindrical start-up heaters 540 are provided in order to preheat the catalyst bed to reaction temperature before introduction of the methane/oxidant gas mixture. Insulation is provided in the annular space between shell 500 and alumina tube 510 which aids in supporting heater 540 and reducing heat losses.

Product tube 550 is provided for withdrawing the reaction gas product mixture. Tube 550 extends to within about 1.0 inches of catalyst bundle 530 and at the bottom is sealed within tube 510. Water cooling coils 560 are provided to aid in quenching the reaction product mixture.

In the runs according to this example, the contact agent bed height is 2.5 inches. The contact agent is prepared as follows:

About 63.50 parts by weight MgO, 6.86 parts by weight LiOH, 17.72 parts by weight $H_3BO_3$ and 43.68 parts by weight $Mn_3O_4$ are ball milled for three hours. To the mixture is added sufficient water to form paste which is suitable for pelletizing.

After 2-3 hours drying at ambient conditions, the catalyst is calcined at 950° C. for 16 hours and then ground to 8 to 14 mesh and 72 grams were loaded in the tube bundle.

Feed gases enter via 570, are preheated and react in catalyst bed 530, and exit via product line 550. Thermocouples are provided (not shown) at a number of locations in the reactor bed.

The reaction gas feed is as follows:
Methane: 5.09 liters/min
Oxygen: 1.16 liters/min
Steam: 6.0 grams/min
$H_2S$: 0.1 cc/min The methane and oxygen flows are measured at 75° F. and 1 atm.

Initially, the methane and air mixture is bypassed around the reactor and nitrogen is introduced at the rate of 100 cc/min via 570 and passes through reactor bed 530 and into line 550 while the bed is electrically preheated by means of heater 540.

When the catalyst temperature reaches 1179° F., the reaction is commenced by diverting the bypassed hydrocarbon and air flows into the reactor; at this time the heaters are set to maintain adiabatic conditions. Reactor pressure is 30 psig., feed gases are 330° F. and exit gases at 1600° F.

Two hours after start of run, methane conversion was 25.0% and $C_2+$ selectivity was 65.0%. Oxygen concentration in the effluent was 0.2%.

EXAMPLE 5

Referring to FIG. 5, the tube bundle 530 is replaced with the metal holder 601 shown in FIG. 6a and 6b. Contact agent is the same as that in Example 4 except that it is ground to 12×14 mesh. Metal holder 601 as shown in FIG. 6 is 310 stainless steel, 3.5 inches thick having six passages of 0.75 inch diameter drilled therethrough. The passages are filled to a height of 2.5 inches with 78 grams of the contact agent, the upper inch of passages 610 having quartz wool placed therein to prevent loss of the contact agent. The contact agent is supported as shown in FIG. 6b.

Metal holder 601 is electrically preheated 1225° F. prior to introducing the feed; the reaction was carried out at 30 psig. Feed gas was:
Methane: 5.09 liters/min
Oxygen: 1.06 liters/min
Steam: 7.0 grams/min
$H_2S$ 0.1 cc/min The feed entered the reactor at 334° F. and the reaction gas mixture exited at 1580° F.

After an hour on stream the methane conversion was 26%, the selectivity to $C_2+$ was 71% and the oxygen concentration in the effluent was 0.1%.

What is claimed is:

1. A method for the oxidative conversion reaction of methane to higher hydrocarbon products and coproduct water wherein a gas mixture comprising methane and a gaseous oxidant is contacted with a solid contact agent in a thin adiabatic reactor bed at reaction conditions, comprising the steps of:
    (1) initially heating the gas mixture to reaction temperature, causing an exothermic reaction in the thin aidabatic reactor bed;
    (2) thereafter passing the said gas mixture at a temperature at least 100° C. less than reaction temperature into said thin adiabatic reactor bed and heating the gas mixture to reaction temperature by conductive flow of heat generated by said exothermic reaction axially through said bed countercurrent to the flow of said mixture; and (3) removing a reaction mixture containing said higher hydrocarbons from said bed.

2. The method of claim 1 wherein the thin bed has and depth of less than 20 inches.

3. The method of claim 1 wherein the thin bed has a depth of less than 8 inches.

4. The method of claim 1 wherein the feed gases are at least 400° C. less than the reaction temperature.

5. The method of claim 1 wherein said solid contact agent is a non-acidic solid.

6. The method of claim 1 wherein said solid contact agent comprises a reducible metal oxide.

7. The method of claim 1 wherein the feed gases contain halogens or chalcogens or both.

* * * * *